United States Patent [19]

Yokogawa et al.

[11] Patent Number: 4,515,891

[45] Date of Patent: May 7, 1985

[54] PROCESS FOR THE PRODUCTION OF DISACCHARIDE-TRIPEPTIDE AND DISACCHARIDE-TETRAPEPTIDE

[75] Inventors: Kanae Yokogawa, Nara; Shozo Kotani, Monoh; Shigeo Kawata, Kobe; Yoshiyuki Takase, Amagasaki, all of Japan

[73] Assignee: Dainippon Pharmaceutical Co., Ltd., Osaka, Japan

[21] Appl. No.: 455,581

[22] Filed: Jan. 4, 1983

[30] Foreign Application Priority Data

Jan. 22, 1982 [JP] Japan ................................. 57-9237

[51] Int. Cl.$^3$ ...................... C12P 21/02; C12P 21/06; C12N 9/48; C12N 9/52
[52] U.S. Cl. ......................................... 435/69; 435/70; 435/212; 435/220
[58] Field of Search ................................. 435/69, 70

[56] References Cited

U.S. PATENT DOCUMENTS 3,929,579 12/1975 Yoshimura et al. ............... 435/188
4,186,194 1/1980 Adam et al. ........................ 429/89

OTHER PUBLICATIONS

Experientia, vol. 32, pp. 677–683 (1976).
Biken Journal, vol. 19, pp. 75–91 (1976).
Agr. Biol. Chem. 39(8), pp. 1533–1543 (1975).

*Primary Examiner*—Alvin E. Tanenholtz
*Attorney, Agent, or Firm*—Wegner & Bretschneider

[57] ABSTRACT

Process for the production of a disaccharide-tripeptide and disaccharide-tetrapeptide which comprises applying an endo-N-acetylmuramidase from *Streptomyces globisporus* and a D-alanyl-meso-2,6-diaminopimelic acid endopeptidase from *Streptomyces nitrosporeus* SK (FERM BP-216) or *Streptomyces globisporus* to hydrolyze cell walls of bacteria such as *Lactobacillus plantarum* and *Corynebacterium diphtheriae*. Said process can give the desired disaccharide-tripeptide and disaccharide-tetrapeptide having excellent pharmacological activities such as immunostimulant activity and potentiating activity of nonspecific resistance to bacterial infections in the form of a single compound (i.e. not mixture thereof) in a high yield.

13 Claims, No Drawings

PROCESS FOR THE PRODUCTION OF DISACCHARIDE-TRIPEPTIDE AND DISACCHARIDE-TETRAPEPTIDE

The present invention relates to a process for the production of disaccharide-tripeptide and disaccharide-tetrapeptide having immunostimulant activity and potentiating activity of nonspecific resistance to bacterial infections.

It is known that peptidoglycans which are structural components of bacterial cell walls have an immunostimulant activity [cf. Experientia, 32, pages 677–683 (1976)]. Many investigators have hitherto tried to obtain water-soluble peptidoglycans having an immunostimulant activity from lytic enzyme digest of bacterial cell walls. However, the water-soluble peptidoglycans obtained by such processes are usually a mixture of various peptidoglycans having various molecular weights, and hence, they have different composition and show different degree of activity in each lot of the preparation.

U.S. Pat. No. 4,186,194 discloses a compound of the formula (I) or (II):

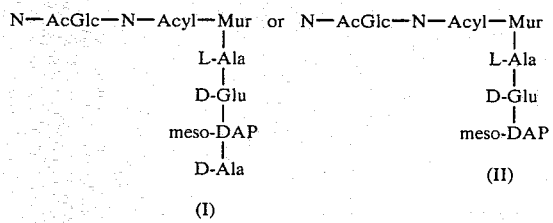

wherein N-AcGlc is N-acetylglucosamyl group, N-Acyl-Mur is N-acylmuramyl group, L-Ala is L-alanyl group, D-Glu is D-glutamyl group, meso-DAP is meso-2,6-diaminopimelyl group or meso-2,6-diaminopimelic acid residue, and D-Ala is D-alanine residue, provided that the carboxyl group in D-glutamic acid and/or meso-2,6-diaminopimelic acid residue may be either in a free state or amidated, in addition to other peptidoglycans having a low molecular weight, wherein it is stated that said compound of the formula (I) or (II) is obtained as a single compound (i.e. not a mixture thereof) and has an immunostimulant activity. The process disclosed in this U.S. patent comprises applying a lytic enzyme to hydrolyze cell walls of Mycobacteria, Nocardiae or *Escherichia coli*. However, they have merely obtained a compound of the formula (I), wherein Acyl is glycolyl group and the carboxyl group of glutamyl and meso-2,6-diaminopimelyl groups is amidated, by hydrolyzing delipidated cell walls by the catalysis of lysozyme and muramyl-L-alanine amidase from Myxobacter $AL_1$ to produce three fractions of peptidoglycans and subjecting one fraction with the lowest molecular weight to preparative electrophoresis. Even in one example wherein insoluble peptidoglycans prepared from cell walls of *E. coli* are hydrolyzed with lysozyme, the fraction with the lowest molecular weight among the three fractions of peptidoglycans comprises a mixture of disaccharide-tetrapeptide and disaccharide-tripeptide. Accordingly, they have never obtained the compound in the form of a single compound.

It is known that Streptomyces sp. L-3 can produce an enzyme: D-alanyl-meso-2,6-diaminopimelic acid endopeptidase (hereinafter, referred to as "endopeptidase") which can specifically split the D-alanyl-meso-2,6-diaminopimelic acid linkages between peptide subunits in bacterial cell wall peptidoglycans [cf. Biken Journal, 19, pages 75–91 (1976)]. As is clear from reference example disclosed hereinafter, however, this strain showed an extremely low producibility of the endopeptidase and could hardly produce the endopeptidase in an amount sufficient for practical use.

It has been reported by the present inventors in Agr. Biol. Chem., 39, pages 1533–1543 (1975) that an endo-N-acetylmuramidase termed M-1 enzyme which hydrolyzes the glycosidic linkages between N-acetylmuramic acid and N-acetylglucosamine, releasing fragments with N-acetylmuramic acid residues at the reducing end, is obtained from mutanolysin which is partially purified from the culture broth of *Streptomyces globisporus* B-1829.

The present inventors have intensively studied an improved process for the production of endopeptidase in an amount sufficient for practical use as a lytic enzyme. As a result, it has been found that the above Streptomyces sp. L-3 can be transformed to *Streptomyces nitrosporeus* SK strain which has an excellent producibility of the desired endopeptidase, that a new endopeptidase having a high activity can be obtained from a culture broth of *Streptomyces globisporus* in a high yield, and further that when the endopeptidase from the mutant: *Streptomyces nitrosporeus* SK or *Streptomyces globisporus* and endo-N-acetylmuramidase from *Streptomyces globisporus* are both applied to hydrolyze certain bacterial cell walls, there can be obtained disaccharide-tripeptide and disaccharide-tetrapeptide in the form of a single compound (i.e. not a mixture thereof).

An object of the present invention is to provide an improved process for producing disaccharide-tripeptide and disaccharide-tetrapeptide having immuno-stimulant activity and potentiating activity of non-specific resistance to bacterial infections in the form of a single compound. Another object of the invention is to provide a process for producing disaccharide-tripeptide and disaccharide-tetrapeptide by applying both enzymes of an endopeptidase and endo-N-acetylmuramidase obtained from specific microorganisms to hydrolyze bacterial cell walls. These and other objects and advantages of the invention will be apparent to persons skilled in the art from the following description.

The present invention provides a process for the production of disaccharide-tripeptide and disaccharide-tetrapeptide of the formula:

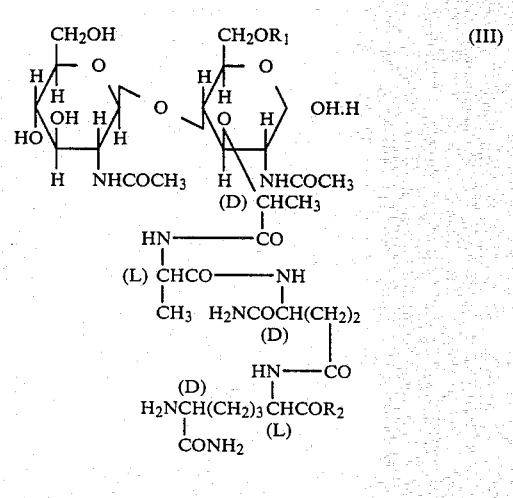

wherein $R_1$ is hydrogen or acetyl group, $R_2$ is hydroxy or a group:

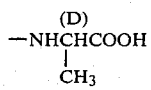

and the marks (D) and (L) mean configuration, which comprises applying an endo-N-acetylmuramidase from *Streptomyces globisporus* and an endopeptidase from *Streptomyces nitrosporeus* SK or *Streptomyces globisporus* to hydrolyze bacterial cell walls which contain a muramic acid moiety wherein the amino group is acetylated, isoglutamine and meso-2,6-diaminopimelic acid having an amidated carboxyl group as constituents of cell wall peptidoglycan, and when a product wherein $R_1$ is acetyl group is obtained, optionally hydrolyzing the product.

According to the present invention, there is obtained the desired water-soluble peptidoglycan of the formula (III) which has high physiological activities with less toxicity in the form of a single compound in a high yield, the chemical structure of said compound being determined.

The compound of the formula (III) includes β-N-acetylglucosaminyl-(1→4)-N-acetylmuramyl-L-alanyl-D-isoglutaminyl-(L)-meso-2,6-diaminopimelic acid-(D)-amide (hereinafter, referred to as "GMP$_3$-A"), β-N-acetylglucosaminyl-(1→4)-N-acetylmuramyl-L-alanyl-D-isoglutaminyl-(L)-meso-2,6-diaminopimelic acid-(D)-amide-(L)-D-alanine (hereinafter, referred to as "GMP$_4$-A"), β-N-acetylglucosaminyl-(1→4)-N,6O-diacetylmuramyl-L-alanyl-D-isoglutaminyl-(L)-meso-2,6-diaminopimelic acid-(D)-amide (hereinafter, referred to as "GMP$_3$-B"), and β-N-acetylglucosaminyl-(1→4)-N,6-O-diacetylmuramyl-L-alanyl-D-isoglutaminyl-(L)-meso-2,6-diaminopimelic acid-(D)-amide-(L)-D-alanine (hereinafter, referred to as "GMP$_4$-B").

Suitable examples of the bacteria used as an origin for the cell walls are *Lactobacillus plantarum, Corynebacterium diphtheriae*, among which the former bacterium is preferable in view of nonpathogenicity thereof. Drug resistant mutants or special structure deficient mutants of these bacteria may be derived from parent strains by using mutagen in order to enhance the content of cell wall peptidoglycans. The starting cell walls can be prepared by cultivating these bacteria in a usual manner, separating the cells from the culture broth, mechanically disrupting the cells, subjecting the disrupted cells to a differential centrifugation, treating the resulting crude cell walls with an aqueous sodium chloride solution of a high concentration in order to remove the intracellular proteins, and treating the cell walls with trypsin in order to remove other proteins. The cell walls thus obtained may further be treated with a 0.05 to 0.5N, preferably 0.1 to 0.2N, aqueous alkali solution to prepare the alkali-treated cell walls, which are also employed as starting cell walls. Alternatively, the alkali-treated cell walls may be prepared by treating firstly whole cells with a 0.05 to 0.5N, preferably 0.1 to 0.2N, aqueous alkali solution and then subjecting the resulting whole cells to the procedure as mentioned above. The treatment with an aqueous alkali solution is usually carried out at room temperature for 30 minutes to 4 hours. Suitable examples of the alkali are alkali metal hydroxides such as lithium hydroxide, sodium hydroxide or potassium hydroxide, and alkali metal carbonates such as sodium carbonate or potassium carbonate.

The cell walls thus obtained are treated with two enzymes, i.e. endo-N-acetylmuramidase and endopeptidase, by which the cell walls are lysed. In this case, it is preferable to firstly treat with the endo-N-acetylmuramidase and then treat with the endopeptidase, or to treat simultaneously with both enzymes. These enzymes should be purified as pure as possible in order to avoid undesirable cleavage of the product.

The endo-N-acetylmuramidase is preferably an enzyme produced by *Streptomyces globisporus* B-1829 (said enzyme is hereinafter referred to as "M$_1$-acetylmuramidase"). This *Streptomyces globisporus* B-1829 is deposited in The Fermentation Research Institute, Agency of Industrial Science and Technology, Japan and The American Type Culture Collection, U.S.A. as FERM-P 596 and ATCC 21553, respectively, and the morphological, cultural and physiological characteristics and culture method of this strain and the method for purifying the enzyme from the culture broth are disclosed in U.S. Pat. No. 3,929,579, and Agr. Biol. Chem., 39, pages 1533–1543 (1975).

The endopeptidase is an enzyme produced by *Streptomyces nitrosporeus* SK or *Streptomyces globisporus* B-1829. The *Streptomyces nitroporeus* SK strain is a mutant possessing high productivity of endopeptidase, which is derived by the present inventors from Streptomyces sp. L-3 described in Biken Journal, 19, pages 75–91 (1976) and is deposited in The Fermentation Research Institute, Agency of Industrial Science and Technology, Japan as FERM BP-216. The derivation (mutation) method, culture method and morphological, cultural and physiological characteristics of the strain and the method for purifying the endopeptidase (hereinafter, referred to as "SK-endopeptidase") from the culture broth are disclosed hereinafter in reference example. The isolation and purification of the endopeptidase from *Streptomyces globisporus* B-1829 (said endopeptidase is hereinafter referred to as "AM$_3$-endopeptidase") is carried out by cultivating the strain and collecting a crude enzyme from the culture broth in the same manner as described in U.S. Pat. No. 3,929,579, and then purifying the crude enzyme in the same manner as described hereinafter in reference example. AM$_3$-endopeptidase is clearly distinguished from SK-endopeptidase in the physicochemical properties and further shows different substrate specificity from that of DD carboxypeptidase produced by *Steptomyces albus* G [cf. Biochemistry, 9, 2955, 2961 (1970)], and hence, this enzyme is a novel endopeptidase.

The lysing treatment of the starting cell walls with two enzymes is usually carried out in a buffer solution of pH 7.0 to 8.5 in the presence of a preservative (e.g. chloroform, sodium nitride, etc.) at about 37° C. The lysing reaction is finished when the amount of reducing sugars liberated attains constant value in case of application of endo-N-acetylmuramidase, and when the amount of free amino groups liberated attains constant value in case of application of endopeptidase. The reaction period of time may vary with amounts of enzymes and amounts and properties of cell walls, but is usually in the range of 8 to 60 hours, preferably 24 to 48 hours. The endopeptidase may be immobilized by a known method (cf. for example, Ichiro Chibata (ed.), "Immobilized Enzyme", Kodansha, Tokyo, 1975) to use continuously. For example, the enzyme can be immobilized by ionic bond on CM-Sephadex C-25 (Na$^+$ type, manufactured by Pharmacia Fine Chemicals AB, Sweden) or by diazo coupling reaction on a diazotized p-aminobenzylcellulose.

Isolation of the desired product from the reaction mixture can be carried out by ion exchange chromatography, column chromatography with silica gel, etc., gel filtration, and the like, which are usually employed in a combination of two or more thereof. When the starting cell walls are those from *Lactobacillus plantarum which are not treated with an alkali*, there are obtained $GMP_3$-A, $GMP_4$-A, $GMP_3$-B and $GMP_4$-B, and when the starting cell walls are the alkali-treated cell walls, there are obtained $GMP_3$-A and $GMP_4$-A. $GMP_3$-B and $GMP_4$-B can quantitatively be converted into $GMP_3$-A and $GMP_4$-A, respectively, by hydrolyzing them under an acidic condition. The hydrolysis can be carried out in a 0.05 to 0.5N, preferably 0.1 to 0.2N, aqueous solution of a mineral acid (e.g. hydrochloric acid) at a temperature of 40° to 80° C., preferably about 60° C., for 2 to 9 hours, preferably 5 to 7 hours.

The compound of the formula (III) can be converted into a salt thereof by treating it with an inorganic base (e.g. sodium hydroxide, potassium hydroxide or ammonium hydroxide), an organic base (e.g. isopropylamine or diethylamine), an inorganic acid (e.g. hydrochloric acid, hydrobromic acid or sulfuric acid), or an organic acid (e.g. methanesulfonic acid) in a usual manner.

The compound of the formula (III) and a pharmaceutically acceptable salt thereof have excellent pharmacological activities such as immunostimulant activity and potentiating activity of nonspecific resistance to bacterial infections and hence are useful for the prophylaxis and treatment of various microbial infections in mammals including human.

The compound of the formula (III) and a pharmaceutically acceptable salt thereof can be administered in oral, parenteral or intrarectal route in the form of a conventional preparation in admixture with conventional carriers or diluents, preferably in parenteral route in the form of an aqueous solution. Dose of the compounds may vary with kinds of the compounds, administration routes, severity of diseases and age of patients, but is usually in the range of 0.001 to 50 mg/kg/day. These compounds may be administered together with other antimicrobial agents, antibiotics or anticancer agents.

The pharmacological activities of $GMP_3$-A, $GMP_4$-A, $GMP_3$-B and $GMP_4$-B were tested as follows.

TEST 1

Immunostimulant activity (immunoadjuvant activity)

The animals sensitized were prepared as follows. Groups of 5 female Hartley strain guinea pigs, weighing 200 to 300 g, were injected in the left hind food-pad with 0.2 ml of a water-in-oil emulsion containing 1 mg of crystalline ovalbumin as antigen and 100 μg of test compound. The water-in-oil emulsion consisted of Drakeol 6VR (Pennsylvania Refining Co., U.S.A.), Arlacel A (Atlas Chemical Industries Inc., U.S.A.) and 1/75M phosphate-buffered physiological saline (pH 7.0) in a ratio of 4:1:5 by volume. Control guinea pigs were injected with a water-in-oil emulsion of similar composition containing the antigen but not test compound (Freund's incomplete adjuvant).

Corneal response

To test for the induction of delayed-type hypersensitivity to ovalbumin, that is, the enhancement of cell-mediated immunity, 2 weeks after the sensitization the guinea pigs were given an intracorneal injection of ovalbumin solution (20 mg/ml saline) to make a transient disc of opacity of approximately 5 mm in diameter. The eyes were examined after 48 hours and the extent and degree of corneal opacity were recorded. The reactions were graded from 3.0, for a strong reaction where the whole cornea was thickened, opaque and grayish-white, to 1.0, where slight opacity was observed. When no visible difference from the uninjected eye was detected, the reaction was graded as 0.

Skin reaction

To test for the induction of delayed-type hypersensitivity to ovalbumin, 3 weeks after the sensitization the guinea pigs were given an intradermal injection of ovalbumin solution (0.1 mg/0.1 ml saline) at one hind footpad shaved with a clipper. The size of induration was measured after 48 hours. The extent of induration was calculated by the formula as described in Biken Journal, 20, pages 95-103 (1977).

Production of humoral antibody

To test for the enhancement of production of humoral antibody, 4 weeks after the sensitization the guinea pigs were bled by cardiac puncture. The levels of antiovalbumin antibody nitrogen were measured quantitatively using a spectrophotometric technique.

The results of the above experiments are shown in Table 1.

TABLE 1

| | Immunostimulant activity | | | | |
|---|---|---|---|---|---|
| | $GMP_3$-A | $GMP_4$-A | $GMP_3$-B | $GMP_4$-B | FIA* |
| Corneal response | 2.2 | 2.0 | 2.4 | 2.2 | 0 |
| Skin reaction | 2.5 | 3.7 | 3.5 | 3.7 | 1.1 |
| Antibody nitrogen (μg/ml) | 350 ± 50 | 399 ± 90 | 250 ± 40 | 216 ± 57 | 26 ± 9 |

*Freund's incomplete adjuvant

TEST 2

Enhancement of nonspecific resistance to bacterial infections

Male Std-ddY strain mice weighing about 23 g were used. Test compounds were dissolved in physiological saline and intravenously administered to the animals 72, 48 and 24 hours before the intraperitoneal infection with *Pseudomonas aeruginosa* No. 12 (inoculum size: $2 \times 10^6$ cells/mouse). The number of survivors were recorded 7 days after the infection. The results are shown in Table 2.

TABLE 2

| | Enhancement of nonspecific resistance to bacterial infections | | | |
|---|---|---|---|---|
| Dose (mg/kg) | Number of survivors/total number of test animals | | | |
| | $GMP_3$-A | $GMP_4$-A | $GMP_3$-B | $GMP_4$-B |
| 12.5 | 16/16 | 16/16 | 16/16 | 16/16 |
| 3.1 | 14/16 | 7/16 | 12/16 | 10/16 |
| 0.8 | 10/16 | 7/16 | 10/16 | 9/16 |
| 0.2 | 8/16 | 4/16 | 9/16 | 6/16 |
| 0.05 | 9/16 | 6/16 | 7/16 | 4/16 |
| 0.0125 | 9/16 | 6/16 | 5/16 | 4/16 |

TABLE 2-continued

| | Enhancement of nonspecific resistance to bacterial infections | | | |
|---|---|---|---|---|
| Dose | Number of survivors/total number of test animals | | | |
| (mg/kg) | GMP$_3$-A | GMP$_4$-A | GMP$_3$-B | GMP$_4$-B |
| 0.0031 | 7/16 | — | — | — |

[Remarks]
The control group to which physiological saline solution is administered: 0/16 —, not done The present invention is illustrated by the following Reference Examples and Examples, wherein "%" is % by weight unless specified otherwise.

REFERENCE EXAMPLE 1

Derivation of *Streptomyces nitrosporeus* SK from Streptomyces sp. L-3

A parent strain of Streptomyces sp. L-3 separated from a soil sample in Kashiwara, Nara, Japan by Kotani et al. [cf. Biken Journal, 3, 139 (1960)] is subjected to repeated subculture for 15 times on a slant medium (pH 7.4) containing a soluble starch (1%), a yeast extract (0.2%), cell walls of *Lactobacillus plantarum* ATCC 8014 (0.1%) and agar (2%), by which the parent strain gets acclimated to the medium.

The parent strain thus treated is cultured on the above medium at 30° C. for 7 days to form spores sufficiently. The spores are taken out with a sterilized physiological saline (5.0 ml), and 0.5 ml of the saline mixture is smeared on the above medium in a Petri dish, and it is cultivated at 30° C. for 4 days. The resulting colonies which are surrounded by large zones of lysis are collected and then transferred to the above slant medium. This procedure is repeated for 15 times, and one strain having particularly excellent producibility of endopeptidase is selected. The strain obtained by the above monocell culture is planted on the above slant medium and is cultivated until spores grow sufficiently. The spores are taken out with a sterilized physiological saline (5.0 ml) and washed twice with physiological saline and then transferred to a Petri dish, which is irradiated with ultraviolet light by a 15 W Toshiba UV sterilizer for 10 minutes at a distance of 15 cm. The resulting solution thus irradiated (0.5 ml) is smeared on the above medium in a Petri dish and cultivated likewise, and thereby a strain having a large zone of lysis compared with the size of colony is collected. This procedure is repeated five times to give the desired SK strain.

The morphological, cultural and physiological characteristics of the new SK strain obtained by the above mutation are shown in Tables 3 to 6.

TABLE 3

| Morphological characteristics | |
|---|---|
| Shape of spore-bearing hyphae | simple branch |
| Surface of spore chain | smooth |
| Number of spores | 10-50 |
| Flagellated spore, sporangium | none |

TABLE 4

| | Cultural characteristics on various media | | | | | | |
|---|---|---|---|---|---|---|---|
| | Growth | | | Aerial mycelium | | | |
| Medium | Vegetation | Shape | Color | Vegetation | Shape | Color | Soluble pigment |
| Yeast extract-malt extract agar medium | good | — | — | thick | — | grayish brown | very scant |
| Oatmeal agar medium | good | spreading | pale yellow green | abundant | — | gray | very scant |
| Inorganic salts-starch agar medium | good | spreading | olive brown | abundant | — | gray | none |
| Glycerol-asparagine agar medium | moderate | raised | pale yellow | — | powdery | pale grayish brown | none |
| Glucose-asparagine agar medium | moderate | raised | pale yellow | scant | — | — | none |
| Tyrosine agar medium | good | — | pale brown | — | cottony | pale gray | pale yellowish brown (trace) |
| Sucrose-nitrate agar medium | scant | — | pale yellow | poor | powdery | — | none |
| Peptone-yeast extract iron agar medium | moderate | wrinkled | colorless | none | — | — | none |
| Starch-yeast extract agar medium | moderate | spreading raised | pale yellow | moderate | powdery | grayish red brown | none |
| Glycerol-calcium maleate agar medium | moderate | spreading | pale yellowish brown | poor | — | — | very scant |
| Gelatin stab | moderate | whorled, grown at bottom | — | none | — | — | dark brown |
| Skim milk medium | moderate | whorled, grown at bottom | — | none | — | — | pale yellowish brown |
| Nitrate liquid medium | moderate | whorled | — | poor | — | — | none |
| Loffler's horse serum medium | moderate | lichenoid | — | none | — | — | dark brown |
| Egg medium | moderate | — | — | none | — | — | dark brown |

[Remarks]
The observation is carried out in the same manner as defined in International Streptomyces Project (ISP) described in Inter. J. Syst. Bacteriol., 16, 313 (1966).
—, not done

TABLE 5

| Physiological characteristics | |
|---|---|
| Test | Results |
| Melanoid pigment production | dark brown pigment in gelatin stab, Loffler's horse serum and egg media; negative on the other media |
| Gelatin liquefaction | positive |
| Milk peptonization | positive |
| H$_2$S production | positive |
| Ca—malate hydrolysis | positive |
| Nitrate reduction | positive |
| Starch hydrolysis | positive |
| Colony reverse side | no change |
| Antibiotic production | negative |
| Endopeptidase produci- | extremely good |

TABLE 5-continued

| Test | Physiological characteristics Results |
|---|---|
| bility | |

TABLE 6

Utilization of carbon sources
(Pridham and Gottlieb agar)

| Sugar | Growth |
|---|---|
| D-Glucose | ++ |
| L-Arabinose | ++ |
| D-Xylose | ++ |
| Inositol | ± |
| D-Mannitol | ± |
| D-Fructose | ++ |
| L-Rhamnose | ± |
| Sucrose | ± |
| Raffinose | ± |
| Salicin | ++ |
| Galactose | ++ |
| Cellulose | ± |

++ good growth,
± poor growth

The cell walls of the above mutant contain L,L-2,6-diaminopimelic acid residue.

Comparing the morphological, cultural and physiological characteristics of the SK strain with the disclosure of Bergey's Manual of Determinative Bacteriology, 8th Edition, the classification of ISP and Hütter System of Streptomyces, there are picked up as related microorganisms *Actinomyces atrolivaceus, Streptomyces halstedii* and *Streptomyces nitrosporeus*. However, *Actinomyces atrolivaceus* is not identified with the present mutant, because it has warty in the surface structure of spore, and *Streptomyces halstedii* is not identified with the present mutant either, because it has 3 to 10 spores. The present mutant is the most resemble to *Streptomyces nitrosporeus*, while both are slightly different from each other in utilization pattern of fructose and rhamnose, and hence, the present mutant is considered to be a new strain of *Streptomyces nitrosporeus* and is designated as SK strain. The SK strain is clearly distinguished from the parent strain in the producibility of endopeptidase as is shown in Table 7.

TABLE 7

Production of endopeptidase (U/ml)

| Culture time (days) | Shake culture | | Stationary culture | |
|---|---|---|---|---|
| | SK strain | Parent strain | SK strain | Parent strain |
| 1 | 0.9 | 0 | 0 | 0 |
| 2 | 2.5 | 0 | 0 | 0 |
| 3 | 2.0 | 0 | 0.1 | 0 |
| 5 | 0.5 | 0 | 0.3 | 0.2 |
| 7 | 0.2 | 0 | 0.4 | 0.3 |
| 9 | 0.1 | 0 | 0.6 | 0.2 |

[Remark]
The figures in the table indicate the lytic activity of the endopeptidase produced. Lytic activity was determined by measuring the rate of reduction of turbidity of a suspension of cell walls of *Lactobacillus plantarum* ATCC 8014. A mixture consisting of adequate amount of the cell wall suspension, Tris-hydrochloric acid buffer (pH 8.0, final concentration of 0.05 M) and aliquot of an enzyme solution in total volume of 4.0 ml was made to give an absorbance of 0.5 at 600 nm and allowed to react in a water bath at 37° C. One unit of lytic activity is defined as the amount of enzyme giving an initial linear decrease in absorbance at 600 nm of 0.001 per minute. The unit of lytic activity of an enzyme solution is calculated according to the following equation:

$$U/ml = \frac{OD_0 - OD_t}{0.001} \times \frac{1}{t} \times \frac{1}{\text{volume of enzyme solution (ml)}}$$

wherein
$OD_0$: optical density of the reaction mixture at zero reaction time,
$OD_t$: optical density after t minute,
t: reaction time (minute) provided that $0.03 \leq OD_0 - OD_t \leq 0.13$.

Both endopeptidases produced by the SK and parent strains show the same mode of action, but it cannot be confirmed whether both enzymes are the same or not because the parent strain has too low producibility of the enzyme. Because of the above reason, the endopeptidase produced by SK strain is designated as SK-endopeptidase and is distinguished from the endopeptidase produced by the parent strain in the present specification.

The SK strain having the above morphological, cultural and physiological characteristics is cultivated in an appropriate medium. The cultivation may be carried out either by shake culture or stationary culture, but is preferably carried out by shake culture at a temperature of 20° to 40° C., more preferably at about 30° C., for 1 to 4 days, more preferably for 2 to 3 days. The medium includes any conventional medium used for culture of microorganisms of genus Streptomyces, for example a medium of pH 6 to 9, preferably 7 to 8, which contains sugars (e.g. glucose, dextrin, maltose, soluble starch), nitrogen sources (e.g. defatted soybean meal, yeast extract, polypeptone, meat extract, corn steep liquor), inorganic salts (e.g. sodium chloride, ammonium sulfate, ammonium chloride, magnesium sulfate, ferric sulfate, zinc sulfate, calcium chloride, calcium carbonate, phosphate), vitamines, or the like. Whole cells or cell walls of some microoganisms such as *Lactobacillus plantarum* or *Corynebacterium diphtheriae* may optionally be added to the medium as an inducer for the formation of SK-endopeptidase.

The isolation of SK-endopeptidase from the culture broth can be carried out by removing cells and insoluble debris from the culture broth and subjecting the resulting solution to treatment with cationic exchange resin, salting-out with ammonium sulfate, and treatment with CM-Sephadex C-25 (Na+ type), which are employed in a combination of two or more thereof.

REFERENCE EXAMPLE 2

Cultivation of *Streptomyces nitrosporeus* SK and preparation of SK-endopeptidase SK strain is inoculated in an amount of 2% in a medium (pH 7.4, 50 liter) containing dextrin (2%), defatted soybean meal (2%), yeast extract (0.5%), sodium chloride (0.2%), and cell walls (0.2%) of *Lactobacillus plantarum* ATCC 8014, and it is cultivated with an aeration rate of 50 liter/minute and a stirring rate of 180 r.p.m., at 30° C. for 3 days, and a filtrate aid (2 kg) is added to the culture broth, and the mixture is filtered through a filter press. To the filtrate (50 liter) is added Amberlite CG-50 (H+ type, manufactured by Rohm and Haas Co., 2.5 kg in wet state), and the mixture is adjusted to pH 5.0 and stirred for one hour. The resin is separated, washed with water, and then eluted with 0.2M aqueous saline (10 liter). The eluate is adjusted to pH 7.5 and to 80% saturation of ammonium sulfate. The resulting precipitates are dissolved in a minimum amount of water and the solution is dialyzed against water at 4° C. for 2 days. The solution is applied to a column (5.6×40 cm) of CM-Sephadex C-25 (Na+ type, manufactured by Pharmacia Fine Chemicals AB, Sweden), which is eluted with a linear gradient at the concentration from 0 to 0.5M of NaCl. The fractions eluted with 0.05 to 0.1M NaCl are pooled, concentrated, desalted and then lyophilized to give SK-endopeptidase (300 mg).

REFERENCE EXAMPLE 3

Preparation of AM$_3$-endopeptidase

*Streptomyces globisporous* B-1829 strain is inoculated in an amount of 1% in a medium (pH 7.5, 70 liter) containing dextrin (2%), defatted soybean meal (0.5%), polypeptone (0.2%), sodium chloride (0.2%), MgSO$_4$ (0.1%), Na$_2$HPO$_4$ (0.5%), and CaCl$_2$ (0.02%), and it is cultivated with an aeration rate of 70 liter/minute and a stirring rate of 250 r.p.m., at 30° C. for 3 days. The culture broth is filtered, and to the filtrate (70 liter) is added Amberlite CG-50 (H$^+$ type, 6.5 kg), and the mixture is stirred for one hour. The resin is separated, washed with water, and then eluted with 0.2M Na$_2$HPO$_4$ (pH 7.5) and the eluate is adjusted to 60% saturation of ammonium sulfate. The resulting precipitates are separated by filtration and dissolved in a small amount of deionized water and the solution is desalted with an electrodialyzer (SELEMION dialyzing cabinet Type DU-Ob, manufactured by Nippon Rensui Co., Japan) for 2 to 5 hours. The resulting solution is applied to a column (5.0×20 cm) of CM-Sephadex C-25 (Na$^+$ type), which is eluted with a linear gradient at the concentration from 0 to 0.06M of NaCl. The active fractions are collected, concentrated, subjected to gel filtration through Sephadex G-25 (manufactured by Pharmacia, Sweden) and then lyophilized to give AM$_3$-endopeptidase (800 mg).

The characteristics of the SK- and AM$_3$-endopeptidases thus obtained are shown in Table 8. The molecular weight of each enzyme is estimated according to SDS-polyacrylamide gel electrophoresis method described in J. Biol. Chem., 246, 6328 (1971). The isoelectric point is determined according to the method described in Acta Chem. Scand., 20, 820 (1966).

TABLE 8

| Characteristics of SK— and AM$_3$—endopeptidase | | |
|---|---|---|
| | SK—endopeptidase | AM$_3$—endopeptidase |
| Source | *Streptomyces nitrosporeus* SK | *Streptomyces globisporus* B-1829 |
| Cultivation condition | aeration | aeration |
| Inducer | necessary | unnecessary |
| pH Stability | stable at pH 5.0–9.5 | stable at pH 7.0–9.0 inactivated below pH 5.0 |
| Optimum pH | pH 9.0 | pH 8.5 |
| Optimum temperature | 55–60° C. | 55–60° C. |
| Optimum concentration of buffer | 0.02 M | 0.04 M |
| Molecular weight | 1.6 × 10$^4$ | 1.3 × 10$^4$ |
| Isoelectric point | pH 8.3 | pH 9.0 |

REFERENCE EXAMPLE 4

Preparation of M$_1$-acetylmuramidase

*Streptomyces globisporus* B-1829 strain is cultivated in a medium (pH 7.5, 70 liter) containing dextrin (2%), defatted soybean meal (0.5%), polypeptone (0.2%), sodium chloride (0.17%), MgSO$_4$ (0.1%), Na$_2$HPO$_4$ (0.5%) and CaCl$_2$ (0.02%) with an aeration rate of 70 liter/minute and a stirring rate of 250 r.p.m., at 30° C. for 3 days. The culture broth is filtered, and to the filtrate (70 liter) is added Amberlite CG-50 (H$^+$ type, 6.5 kg), and the mixture is stirred for one hour and filtered. The separated resin is eluted with 0.2M Na$_2$HPO$_4$ (pH 7.5), and the eluate is adjusted to 60% saturation of ammonium sulfate. The resulting precipitates are separated by filtration and dissolved in a small amount of deionized water. The solution is applied to a column (3.0×70 cm) of CM-cellulose (Na$^+$ type, manufactured by Bio-Rad Laboratories, U.S.A.) equilibrated with 0.05M phosphate buffer (pH 7.0). The elution is carried out stepwise with 0.05M and 0.1M phosphate buffer (pH 7.0). The fraction eluted with 0.1M phosphate buffer is dialyzed against water and applied to a column (3.0×60 cm) of CM-Sephadex C-25 (Na$^+$ type) equilibrated with 0.05M phosphate buffer, which is eluted stepwise with 0.05M and 0.1M phosphate buffer (pH 7.0). The fraction eluted with 0.1M phosphate buffer is dialyzed against 0.05M phosphate buffer (pH 7.0). The dialyzed solution is subjected to gel filtration through Sephadex G-75 (manufactured by Pharmacia, Sweden), and the obtained active fraction is desalted, concentrated and then lyophilized to give M$_1$-acetylmuramidase (1,100 mg).

REFERENCE EXAMPLE 5

Preparation of cell walls

Wet whole cells (520 g) of *Lactobacillus plantarum* ATCC 8014 are suspended in physiological saline (4 liter) and are disrupted with DYNO-Laboratory Mill (manufactured by Shinmaru Enterprises Corporation, Japan). The mixture is centrifuged (800×g, 10 minutes) to remove the undisrupted cells, and to the supernatant is added sodium chloride in a concentration of 1M. The cell walls are harvested by a centrifuge (9,000×g, 30 minutes), washed with a large amount of deionized water and collected by centrifugation. This treatment is repeated three times. The washed cell walls are suspended in 0.05M phosphate buffer (pH 7.0), and thereto is added trypsin (4.2 g), and the mixture is allowed to stand at 37° C. for 6 hours. The reaction mixture is cooled and centrifuged (800×g, 15 minutes) to remove insoluble debris, and the supernatant is further centrifuged (9,000×g, 30 minutes) to collect cell walls. The cell walls are washed with 0.05M phosphate buffer (pH 7.0) and collected by centrifugation. This treatment is repeated two times to give purified cell walls (86 g).

REFERENCE EXAMPLE 6

Preparation of alkali-treated cell walls

The cell walls (80 g) obtained in Reference Example 5 are suspended in 0.1N NaOH (4.4 liter) and the suspension is stirred at room temperature for 30 minutes to 2 hours, neutralized with a concentrated hydrochloric acid and then centrifuged (9,000×g, 30 minutes) to collect cell walls. The cell walls are washed with 1M saline solution and water and then lyophilized to give alkali-treated cell walls (40 g).

REFERENCE EXAMPLE 7

Preparation of alkali-treated cell walls

Wet whole cells (121 g) of *Lactobacillus plantarum* ATCC 8014 are well suspended in tap water (1 liter) and thereto is added solid NaOH (4 g). After NaOH is dissolved completely, the mixture is stirred at room temperature for 30 minutes. The mixture is adjusted to about pH 7.0 with a concentrated hydrochloric acid and centrifuged (800×g, 10 minutes), and the resulting precipitates are washed with water (one time). The alkali-treated whole cells thus obtained are treated in the same manner as described in Reference Example 5 to give alkali-treated cell walls (18 g).

REFERENCE EXAMPLE 8

Immobilization of $AM_3$-endopeptidase $AM_3$-endopeptidase (500 mg) obtained in Reference Example 3 is dissolved in 0.05M phosphate buffer (pH 8.0, 20 ml), and the solution is added to p-aminobenzyl-cellulose (1,000 mg) which is diazotized in a usual manner, and the mixture is stirred at 4° C. for 20 hours and thereafter is incubated at 37° C. for one hour. After the reaction is finished, the immobilized enzyme is separated by filtration and washed with 0.25M phosphate buffer (pH 8.0) and water to remove free enzyme. The immobilized enzyme thus obtained is kept at low temperature.

REFERENCE EXAMPLE 9

Immobilization of $AM_3$-endopeptidase $AM_3$-endopeptidase (200 mg) obtained in Reference Example 3 is further purified by subjecting it to gel filtration through a column (2.0×100 cm) of Sephadex G-100. The purified enzyme is added to a suspension of CM-Sephadex C-25 ($Na^+$ type, 5.0 g in wet state) in 0.001M phosphate buffer (pH 6.5, 50 ml), and the mixture is stirred at 4° C. for 24 hours. The CM-Sephadex C-25 is separated by filtration and washed well with the above buffer (500 ml) to give $AM_3$-endopeptidase-linked CM-Sephadex C-25.

EXAMPLE 1

Preparation of $GMP_3$-A, $GMP_4$-A, $GMP_3$-B and $GMP_4$-B

The purified cell walls (43 g) obtained in Reference Example 5 are suspended in Tris-hydrochloric acid buffer (pH 8.5, final concentration of 0.02M) and are dispersed well with a sonication and then heat-treated at 120° C. for 10 minutes. After cooling, $M_1$-acetyl-muramidase (43 mg) obtained in Reference Example 4 and sodium nitride (280 mg) are added to the suspension, and thereto is further added deionized water to make total volume of 4.3 liter. The mixture is incubated at 37° C. for 24 hours. SK-endopeptidase (105 mg) obtained in Reference Example 2 is added to the mixture, and the resulting mixture is stirred at the same temperature for 24 hours and then heated at 100° C. for 2 minutes in order to terminate the reaction. The reaction mixture is cooled and centrifuged (9,000×g, 30 minutes) to remove insoluble materials, and the supernatant is passed through a column (5.6×50 cm) of EC-TEOLA-cellulose (manufactured by Brown Co., U.S.A.), and the unadsorbed fraction is concentrated under reduced pressure below 50° C. The concentrated solution is passed through a Sephadex G-50 column (5.6×83 cm) connected in series with a Sephadex G-25 column (5.6×77 cm), and the fractions containing medium molecular weight substances are collected and concentrated under reduced pressure below 50° C. The concentrated solution is treated with Dowex 50W×2 ($Na^+$ type, manufactured by Dow Chemical Co., U.S.A.), and the unadsorbed frasction is concentrated likewise. The concentrated solution is applied to a column of silica gel (7×70 cm) and developed with 70% propanol (700 ml) and the fractions containing $GMP_3$-A, $GMP_4$-A, $GMP_3$-B and $GMP_4$-B are collected and concentrated. The concentrated solution is further applied to a nylon column of silica gel (7×80 cm), and developed with isobutyric acid—0.5M $NH_4OH$ (5:3 V/V). The column is cut in a fixed length. A part of each portion is extracted with the same solvent as above and the extract is subjected to thin layer chromatography (TLC) and developed with the solvent. It is monitored which portion contains the peptidoglycans. Two groups of portions containing a peptidoglycan homogeneous on TLC are each collected and are washed with ether to remove isobutyric acid and then extracted with water. The extract is concentrated and desalted by gel filtration. The fraction containing a mixture of $GMP_3$-A and $GMP_4$-A and the fraction containing a mixture of $GMP_3$-B and $GMP_4$-B are each subjected to chromatography on a column (4.5×30 cm) of CM-Sephadex C-25 ($H^+$ type), which is eluted with $0.5×10^{-3}N$ hydrochloric acid (2.0 liter) to separate into each fraction of $GMP_3$-A, $GMP_4$-A, $GMP_3$-B and $GMP_4$-B. The fractions containing predominantly each compound are collected and are each neutralized carefully with 0.01N NaOH and concentrated under reduced pressure below 50° C. Each concentrated solution is desalted by gel filtration through a column (5.0×80 cm) of Sephadex G-25, concentrated under reduced pressure below 50° C. and lyophilized to give $GMP_3$-A, $GMP_4$-A, $GMP_3$-B and $GMP_4$-B in an amount of 0.7 g, 0.7 g, 1.6 g and 1.4 g, respectively.

The physicochemical properties and chemical analysis of these four compounds are shown in Table 9.

TABLE 9

Physicochemical properties and chemical analysis of each compound

| | | $GMP_3$—A | | | $GMP_4$—A | | | $GMP_3$—B | | | $GMP_4$—B | | |
|---|---|---|---|---|---|---|---|---|---|---|---|---|---|
| Appearance | | white powder | | | | | | | | | | | |
| Solubility | | Soluble in water, 50% $C_{1-3}$ alcohol; insoluble in diethyl ether | | | | | | | | | | | |
| Specific rotation $[\alpha]_D^{25}$ | | −7.8° | | | −11.4° | | | +4.7° | | | −1.2° | | |
| (c = 1.0, water, after 24 hours) | | | | | | | | | | | | | |
| Molecular formula | | $C_{34}H_{58}O_{18}N_8 \cdot 5H_2O$ | | | $C_{37}H_{63}O_{19}N_9 \cdot 6H_2O$ | | | $C_{36}H_{60}O_{19}N_8 \cdot 3/2H_2O$ | | | $C_{39}H_{65}O_{20}N_9 \cdot 2H_2O$ | | |
| Elemental anaylsis | | C | H | N | C | H | N | C | H | N | C | H | N |
| calculated | | 42.68 | 7.11 | 11.72 | 42.49 | 7.18 | 12.06 | 46.20 | 6.78 | 11.97 | 46.10 | 6.87 | 12.41 |
| found | | 42.94 | 7.17 | 11.78 | 42.39 | 6.93 | 11.78 | 46.50 | 6.91 | 11.95 | 45.97 | 6.66 | 12.36 |
| Analysis of | Glucosamine | 0.90 | | | 0.94 | | | 0.83 | | | 0.85 | | |
| amino sugar | Muramic acid | 1.08 | | | 1.06 | | | 0.91 | | | 0.89 | | |
| and amino | Glutamic acid | (1.00) | | | (1.00) | | | (1.00) | | | (1.00) | | |
| acid* | Alanine | 1.11 | | | 2.14 | | | 1.13 | | | 2.16 | | |
| | Diaminopimelic acid | 1.20 | | | 1.18 | | | 1.20 | | | 1.19 | | |
| C-terminal amino acid | | diaminopimelic acid | | | alanine | | | diaminopimelic acid | | | alanine | | |

TABLE 9-continued

| Physicochemical properties and chemical analysis of each compound | | | | |
|---|---|---|---|---|
| | GMP$_3$—A | GMP$_4$—A | GMP$_3$—B | GMP$_4$—B |
| N-terminal amino acid | | diaminopimelic acid | | |

*The data are shown as molar ratio to total glutamic acid residue.

The four compounds are each hydrolyzed with N-acetylmuramyl-N-alanine amidase isolated from *Streptomyces globisporus* B-1829 to give degradation products as shown in Table 10. The analytical data of these degradation products are also shown in Table 10. The analysis is carried out by a known method as described in Biochemistry, 5, 3079 (1966); ibid., 6, 921 (1967); and Biochem. Biophys. Res. Comm., 40, 57 (1970), and the chemical structure thereof is determined by instrumental analysis (MS, GCMS, NMR, IR, UV) and enzymatic analysis.

eluted with methanol (10 liter) to give a fraction containing a mixture of GMP$_3$-A and GMP$_4$-A. Both fractions are each concentrated under reduced pressure below 50° C. and are each applied to a column (20×135 cm) of Diaion HP-20 (manufactured by Mitsubishi Chemical Industries Co., Ltd., Japan). When the columns are each eluted with tap water (10 liter) and then with 5% methanol (10 liter), there are obtained GMP$_3$-A and GMP$_3$-B from the fraction eluted with water, and GMP$_4$-A and GMP$_4$-B from the fraction eluted with 5% methanol. Each fraction of GMP$_3$-A, GMP$_4$-

TABLE 10

| | Analytical results of degradation product | | | |
|---|---|---|---|---|
| | GMP$_3$—A | GMP$_4$—A | GMP$_3$—B | GMP$_4$—B |
| Degradation product by catalysis of N—acetylmuramyl-L-alanine amidase | N—AcGlc—N—AcMur, tripeptide | N—AcGlc—N—AcMur, tetrapeptide | N—AcGlc—N,6-O—diAcMur, tripeptide | N—AcGlc—N,6-O—diAcMur, tetrapeptide |
| Peptide fraction: Amino acid sequence (Edman degradation) | L-Ala—D-isoGln—meso-A$_2$pm | L-Ala—D-isoGln—meso-A$_2$pm-D-Ala | L-Ala—D-isoGln—meso-A$_2$pm | L-Ala—D-isoGln—meso-A$_2$pm-D-Ala |
| Sugar fraction: Degradation product by catalysis of exo-β-N—acetylglucosamidase* | N—AcGlc, N—AcMur | | N—AcGlc, N,6-O—diAcMur | |
| O—Acetyl group | — | | + | |
| Glycosidic bond | | β-1,4-linked | | |
| Reducing sugar | | N—AcMur | | N,6-O—diAcMur |

The abbreviations are as follows:
N—AcGlc—N—AcMur, β-N—acetylglucosaminyl-(1→4)-N—acetylmuramic acid;
N—AcGlc—N,6-diAcMur, β-N—acetylglucosaminyl-(1→4)-N,6-O—diacetylmuramic acid;
L-Ala—D-isoGln—meso-A$_2$pm, L-alanyl-D-isoglutaminyl-(L)-meso-2,6-diaminopimelic acid-(D)-amide;
L-Ala—D-isoGln—meso-A$_2$pm-D-Ala, L-alanyl-D-isoglutaminyl-(L)-meso-2,6-diaminopimelic acid-(D)-amide-(L)-D-alanine;
N—AcGlc, N—acetylglucosamiNe; N—AcMur, N—acetylmuramic acid; and
N,6-O—diAcMur, N,6-O—diacetylmuramic acid.
*cf. Biochem. J., 77, 170 (1960)

EXAMPLE 2

Preparation of GMP$_3$-A, GMP$_4$-A, GMP$_3$-B and GMP$_4$-B

The purified cell walls (1,200 g) of *Lactobacillus plantarum* ATCC 8014 obtained by the method of Reference Example 5 are suspended in a phosphate buffer (pH 8.0, final concentration of 0.04M; 30 liter) and thereto are added M$_1$-acetylmuramidase (2.4 g), chloroform (50 ml), CoCl$_2$.6H$_2$O (14.3 g), AM$_3$-endopeptidase (0.58 g) and further tap water to make total volume of 60 liter. The mixture is stirred at 37° C. for 24 hours. The reaction mixture is adjusted to pH 2.5–3.0 with a concentrated hydrochloric acid and centrifuged to remove insoluble materials. The supernatant is carefully neutralized with a dilute NaOH solution and is passed through a column (10×140 cm) of Diaion PA 316 (Cl$^-$ type, manufactured by Mitsubishi Chemical Industries Co., Ltd., Japan) to remove impurities. The unadsorbed fraction is applied to a column (14×190 cm) of Diaion PK 212 (H$^+$ type, manufactured by Mitsubishi Chemical Industries Co., Ltd., Japan), which is eluted with 0.3M saline solution. The eluate is carefully neutralized with a dilute NaOH solution and is applied to a column (5.0×50 cm) of silica gel (Kieselgel 60F$_{254}$, manufactured by E. Merck AG, West Germany). The column is washed with chloroform-methanol-water (15:10:2 V/V; 10 liter) and is eluted with chloroform-methanol-water (10:10:2 V/V; 15 liter) to give a fraction containing a mixture of GMP$_3$-B and GMP$_4$-B, and thereafter is A, GMP$_3$-B and GMP$_4$-B is concentrated under reduced pressure below 50° C. and is applied to a column (15×135 cm) of CM-Sephadex (H$^+$ type), which is eluted with 0.5×10$^{-3}$N hydrochloric acid (10 liter). The eluate is neutralized with a dilute NaOH solution, concentrated under reduced pressure below 50° C. and desalted by gel filtration through a column (6.0×160 cm) of Sephadex G-25. The solution is concentrated under reduced pressure below 50° C. and lyophilized to give GMP$_3$-A, GMP$_4$-A, GMP$_3$-B and GMP$_4$-B in an amount of 38 g, 38 g, 67.8 g and 56.2 g, respectively.

EXAMPLE 3

Preparation of GMP$_3$-A and GMP$_4$-A

The alkali-treated cell walls (1,200 g) of *Lactobacillus plantarum* ATCC 8014 obtained by the method of Reference Example 6 are suspended in a phosphate buffer (pH 8.5, final concentration of 0.02M; 30 liter) and dispersed well. The suspension is mixed with M$_1$-acetylmuramidase (2.4 g), chloroform (50 ml), CoCl$_2$.6H$_2$O (14.3 g) and the immobilized AM$_3$-endopeptidase (1.0 g in dry state) obtained in Reference Example 8 and thereto is added tap water to make total volume of 60 liter. The mixture is stirred at 37° C. for 48 hours. The immobilized enzyme is removed from the reaction mixture with a dehydrator. The supernatant is adjusted to pH 2.5–3.0 with a concentrated hydrochloric acid, and the resulting precipitates are removed by centrifugation at a high speed. The supernatant is carefully neutralized with a dilute NaOH solution and is passed through a column (10×140 cm) of Diaion PA 316 (Cl⁻ type) to remove impurities. The unadsorbed fraction is further applied to a column (14×190 cm) of Diaion PK 212 (H+ type), which is eluted with 0.3M saline solution. The eluate is neutralized with a dilute NaOH solution and applied to a colunm (20×135 cm) of Diaion HP-20, which is eluted with water to give a fraction of GMP₃-A and then with 5% methanol to give a fraction of GMP₄-A. Each fraction of GMP₃-A and GMP₄-A thus obtained is desalted and concentrated with a reverse osmosis instrument (RO-Module RT-1, manufactured by Sumitomo Chemical Co., Ltd., Japan), and thereafter, they are each applied to a column (15×135 cm) of CM-Sephadex (H+ type), which is eluted with 0.001N hydrochloric acid (10 liter). The eluate is neutralized with a dilute NaOH solution, concentrated under reduced pressure below 50° C. and then desalted by gel filtration through a column (6.0×160 cm) of Sephadex G-25. The eluate thus obtained is concentrated under reduced pressure below 50° C. and lyophilized to give GMP₃-A and GMP₄-A in an amount of 110 g and 90 g, respectively.

EXAMPLE 4

Preparation of GMP₃-A and GMP₄-A

The alkali-treated cell walls (1,200 g) of *Lactobacillus plantarum* ATCC 8014 obtained by the method of Reference Example 7 are suspended in a phosphate buffer (pH 8.5, final concentration of 0.02M; 30 liter) and dispersed well. The suspension is mixed with M₁-acetylmuramidase (2.4 g) and chloroform (50 ml), and thereto is added tap water to make total volume of 60 liter. The mixture is stirred at 37° C. for 24 hours. The reaction mixture is adjusted to pH 2.5–3.0 with a concentrated hydrochloric acid, and the resulting precipitates are removed by centrifugation at a high speed. The supernatant is neutralized with a concentrated NaOH solution and passed through a column (10×140 cm) of Diaion PA 316 (Cl⁻ type) to remove the impurities. The unadsorbed fraction is desalted with an electrodialyzer (SELEMION dialyzing cabinet Type DU-Ob) and then adjusted to pH 6.5 with hydrochloric acid. AM₃-endopeptidase-linked CM-Sephadex C-25 obtained by the method of Reference Example 9 is packed into a column (10×100 cm), through which the above solution is passed at a flow rate of 100 ml/minute while keeping at 37° C. This procedure is repeated two to three times. The reaction mixture thus obtained is applied to a column (14×190 cm) of Diaion PK 212 (H+ type), which is eluted with 0.3M saline solution (20 liter). The eluate is neutralized with a dilute NaOH solution and is applied to a column (20×135 cm) of Diaion HP-20. Thereafter the same treatment as described in Example 3 is carried out to give GMP₃-A and GMP₄-A in an amount of 100 g and 80 g, respectively.

EXAMPLE 5

Conversion of GMP₃-B and GMP₄-B into GMP₃-A and GMP₄-A

GMP₃-B (1,000 mg) is dissolved in 0.1N hydrochloric acid (10 ml) and the solution is heated at 60° C. for 8 hours. After cooling, the reaction mixture is adjusted to pH 6.0 with a dilute NaOH solution and is concentrated under reduced pressure below 50° C. and then desalted by gel filtration through a column of Sephadex G-25.

The eluate is concentrated under reduced pressure below 50° C. and lyophilized to give GMP₃-A (960 mg).

GMP₄-B (1,000 mg) is treated in the same manner as described above to give GMP₄-A (966 mg).

What is claimed is:

1. A process for the production of a disaccharide-tripeptide and disaccharide-tetrapeptide of the formula:

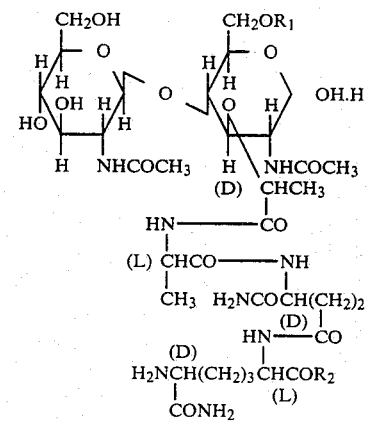

wherein R₁ is hydrogen or acetyl, R₂ is hydroxy or

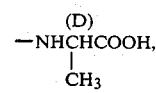

and (D) and (L) designate configuration, which comprises applying a purified endo-N-acetylmuramidase from *Streptomyces globisporus* and a purified D-alanyl-meso-2,6-diaminopimelic acid endopeptidase from *Streptomyces nitroporeus* SK (FERM BP-216) or *Streptomyces globisporus*, to hydrolyze selectively cell walls of *Lactobacillus plantarum* or *Corynebacterium diphtheriae*, which cell walls contain a muramic acid moiety wherein the amino group is acetylated, isoglutamine and meso-2,6-diaminopimelic acid having an amidated carboxyl group as constituents of cell wall peptidoglycan, and isolating the resultant product in the form of a single compound.

2. A process according to claim 1, wherein said *Streptomyces globisporus* is *Streptomyces globisporus* B-1829 (ATCC 21553).

3. A process according to claim 1, wherein the cell walls are treated with alkali prior to hydrolysis.

4. A process according to claim 1, wherein when R₁ is acetyl, hydrolyzing the product prior to isolation.

5. A process for the production of a disaccharide-tripeptide and disaccharide-tetrapeptide of the formula:

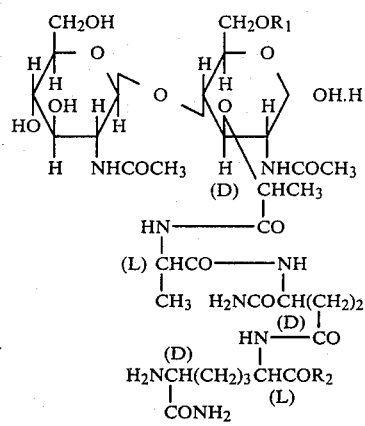

wherein $R_1$ is hydrogen or acetyl, $R_2$ is hydroxy or

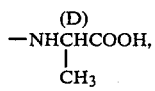

and (D) and (L) designate configuration, which comprises applying a purified endo-N-acetylmuramidase from *Streptomyces globisporus* B-1829 (ATCC 21553) and a purified D-alanyl-meso-2,6-diaminopimelic acid endopeptidase from *Streptomyces nitrosporeus* SK (FERM BP-216) or *Streptomyces globisporus* B-1829 (ATCC 21553), to hydrolyze selectively cell walls of *Lactobacillus plantarum* or *Corynebacterium diphtheriae,* and isolating the resultant product in the form of a single compound.

6. A process according to claim 5, wherein the resultant product is β-N-acetylglycosaminyl-(1→4)-N-acetylmuramyl-L-alanyl-D-isoglutaminyl-(L)-meso-2,6-diaminopimelic acid-(D)-amide, β-N-acetylglucosaminyl-(1→4)-N-acetylmuramyl-L-alanyl-D-isoglutaminyl-(L)-meso-2,6-diaminopimelic acid-(D)-amide-(L)-D-alanine, β-N-acetylglucosaminyl-(1→4)-N,6-O-diacetylmuramyl-L-alanyl-D-isoglutaminyl-(L)-meso-2,6-diaminopimelic acid-(D)-amide, or β-N-acetylglucosaminyl-(1→4)-N,6-O-diacetylmuramyl-L-alanyl-D-isoglutaminyl-(L)-meso-2,6-diaminopimelic acid-(D)-amide-(L)-D-alanine.

7. A process according to claim 5, wherein when $R_1$ is acetyl, hydrolyzing the product prior to isolation.

8. A process according to claim 7, wherein the resultant product is β-N-acetylglucosaminyl-(1→4)-N-acetylmuramyl-L-alanyl-D-isoglutaminyl-(L)-meso-2,6-diaminopimelic acid-(D)-amide or β-N-acetylglucosaminyl-(1→4)-N-acetylmuramyl-L-alanyl-D-isoglutaminyl-(L)-meso-2,6-diaminopimelic acid-(D)-amide-(L)-D-alanine.

9. A process according to claim 5, wherein the cell walls are treated with alkali prior to hydrolysis.

10. A process according to claim 9, wherein the alkali-treated cell walls are treated with alkali by treating the cell walls with a 0.05 to 0.5N aqueous solution of an alkali or by treating whole cells with a 0.05 to 0.5N aqueous solution of an alkali and then separating the cell walls.

11. A process according to claim 10, wherein the aqueous alkali solution has a concentration of 0.1 to 0.2N.

12. A process according to claim 11, wherein the alkali is a member selected from the group consisting of an alkali metal hydroxide and an alkali metal carbonate.

13. A process according to claim 9, wherein the resultant product is β-N-acetylglucosaminyl-(1→4)-N-acetylmuramyl-L-alanyl-D-isoglutaminyl-(L)-meso-2,6-diaminopimelic acid-(D)-amide or β-N-acetylglucosaminyl-(1→4)-N-acetylmuramyl-L-alanyl-D-isoglutaminyl-(L)-meso-2,6-diaminopimelic acid-(D)-amide-(L)-D-alanine.

* * * * *